(12) United States Patent
Hancock

(10) Patent No.: US 9,236,646 B2
(45) Date of Patent: Jan. 12, 2016

(54) SURGICAL ANTENNA STRUCTURE

(75) Inventor: Christopher Paul Hancock, Bristol (GB)

(73) Assignee: CREO MEDICAL LIMITED, Somerset (GB)

( * ) Notice: Subject to any disclaimer, the term of this patent is extended or adjusted under 35 U.S.C. 154(b) by 919 days.

(21) Appl. No.: 13/379,623

(22) PCT Filed: Jul. 20, 2010

(86) PCT No.: PCT/GB2010/001371
§ 371 (c)(1),
(2), (4) Date: Dec. 20, 2011

(87) PCT Pub. No.: WO2011/010086
PCT Pub. Date: Jan. 27, 2011

(65) Prior Publication Data
US 2012/0101492 A1    Apr. 26, 2012

(30) Foreign Application Priority Data

Jul. 20, 2009 (GB) .................................. 0912576.6

(51) Int. Cl.
*H01Q 1/22* (2006.01)
*A61B 18/18* (2006.01)
(Continued)

(52) U.S. Cl.
CPC *H01Q 1/22* (2013.01); *A61B 18/18* (2013.01); *A61B 18/1815* (2013.01); *H01Q 1/38* (2013.01);
(Continued)

(58) Field of Classification Search
CPC .... A61B 18/18; A61B 18/1815; A61B 18/14; A61B 2018/1876; A61B 2018/1892; H01Q 1/22; H01Q 1/38; H01Q 13/08
See application file for complete search history.

(56) References Cited

U.S. PATENT DOCUMENTS 5,057,106 A * 10/1991 Kasevich et al. ............... 606/33
6,287,302 B1  9/2001 Berube
(Continued)

FOREIGN PATENT DOCUMENTS

EP  1 810 625 A1  7/2007
EP  2 106 763 A1  10/2009
(Continued)

OTHER PUBLICATIONS

Walter Buck, "Slotted Cylinder Antenna for Selective Electromagnetic Heating Inside the Human Body", European Microwave Conference 1978, pp. 548-552.
(Continued)

*Primary Examiner* — Christopher D Koharski
*Assistant Examiner* — Frances Oropeza
(74) *Attorney, Agent, or Firm* — Arent Fox LLP

(57) ABSTRACT

A surgical spatula has a planar transmission line for carrying microwave energy formed from a sheet of a first dielectric material which has first and second conductive layers on opposite sides thereof. The surgical spatula also has a coaxial cable for delivering microwave energy to the planar transmission line. The coaxial cable has an inner conductor, an outer conductor coaxial with the inner conductor and a second dielectric material separating the inner and outer conductors. The inner and outer conductors extend beyond the second dielectric to overlap opposite surfaces of the transmission line and electrically contact the first conductive layer and second conductive layer respectively. The width of the first and second conductive layers is selected to create an impedance match between the transmission line and the coaxial cable.

17 Claims, 10 Drawing Sheets

(51) Int. Cl.
 *H01Q 1/38* (2006.01)
 *H01Q 13/08* (2006.01)
 *A61B 18/14* (2006.01)

(52) U.S. Cl.
 CPC ............... *H01Q 13/08* (2013.01); *A61B 18/14* (2013.01); *A61B 2018/1876* (2013.01); *A61B 2018/1892* (2013.01)

(56) References Cited

U.S. PATENT DOCUMENTS

| | | | |
|---|---|---|---|
| 2005/0203499 | A1 | 9/2005 | Pendekanti et al. |
| 2005/0273097 | A1 | 12/2005 | Ryan |
| 2006/0081565 | A1 | 4/2006 | Lee et al. |
| 2008/0221650 | A1 | 9/2008 | Turner et al. |
| 2010/0004650 | A1 | 1/2010 | Ormsby et al. |
| 2010/0286687 | A1* | 11/2010 | Feldberg et al. ............ 606/33 |
| 2010/0331838 | A1 | 12/2010 | Ibrahim et al. |

FOREIGN PATENT DOCUMENTS

| | | | |
|---|---|---|---|
| EP | 2 174 613 | A1 | 4/2010 |
| EP | 2 255 742 | A1 | 12/2010 |
| GB | 2472012 | A | 1/2011 |
| GB | 2472972 | A | 3/2011 |
| JP | 62-1605 | U | 1/1987 |
| JP | 4-323905 | A | 11/1992 |
| JP | 09-140723 | A | 6/1997 |
| JP | 2004-024787 | A | 1/2004 |
| JP | 2005-34653 | A | 2/2005 |
| WO | WO 98/19613 | A1 | 5/1998 |
| WO | WO 03/039385 | A2 | 5/2003 |
| WO | WO 2004/047659 | A2 | 6/2004 |
| WO | WO 2006/111192 | A1 | 10/2006 |
| WO | WO 2006/111192 | A1 | 10/2006 |
| WO | WO 2006/127847 | A2 | 11/2006 |
| WO | WO 2008/043997 | A1 | 4/2008 |
| WO | WO 2008/044000 | A1 | 4/2008 |
| WO | WO 2008/044000 | A1 | 4/2008 |
| WO | WO 2009/062057 | A2 | 5/2009 |
| WO | WO 2011/010086 | A1 | 1/2011 |

OTHER PUBLICATIONS

Paglione, Robert W. et al., "Microwave Applicators for Localized Hyperthermia Treatment of Malignant Tumors." IEEE MTT-S International Microwave Symposium Digest 1980 IEEE, May 28, 1980 May 30, 1980 pp. 351-354.

* cited by examiner

SURGICAL ANTENNA STRUCTURE

CROSS-REFERENCE TO RELATED APPLICATION

This application is a National Stage entry of International Application No. PCT/GB2010/001371, filed Jul. 20, 2010, which claims priority to GB Patent Application No. 0912576.6, filed Jul. 20, 2009. The disclosures of the prior applications are each hereby incorporated in their entirety by reference herein.

FIELD OF THE INVENTION

The invention relates to surgical antenna structures which use microwave radiation to treat biological tissue. For example, the invention may be applied to antennas sized to be suitable for insertion through the instrument channel of a standard surgical endoscope.

BACKGROUND TO THE INVENTION

At certain frequencies, microwave energy can produce controlled ablation of biological tissue. For example, microwave energy having a frequency between 14 and 15 GHz has a relatively limited depth of penetration into biological tissue, which is beneficial for ablation control.

WO 2004/047659 and WO 2005/115235 disclose apparatus for and methods of both controllably ablating biological tissue and measuring information about tissue type and/or state using microwave radiation. These documents disclose the benefits of performing dynamic impedance matching between the energy source and the tissue.

WO 2008/044000 discloses a radiating scalpel suitable for use with the ablation apparatus mentioned above. The scalpel comprising an antenna arranged to emit a substantially uniform microwave radiation field along the cutting edge (i.e. blade) of the scalpel. The emitted microwave radiation is able to cauterise biological tissue during cutting, which facilitates invasive surgery performed on highly vascularised organs such as the liver.

SUMMARY OF THE INVENTION

At its most general, the present invention proposes a particular configuration for a surgical spatula that enables it to radiate microwave energy from one or more of its edges (sides and/or ends) or faces (top and/or bottom). In particular, the configuration is arranged to ensure efficient transfer of energy into biological tissue when in contact with that tissue and efficient isolation of energy when in air (i.e. preventing radiation into free space) or in tissue structures that are not of interest, i.e. healthy tissue structures.

A spatula is a different type of surgical tool from the scalpel disclosed in WO 2008/044000. A spatula is typically characterised by a flat paddle that extends away from a handle. In the invention, the front edge of the paddle (i.e. the edge at a side opposite the handle) is rounded (i.e. blunt) to facilitate safe insertion of the spatula into the body, e.g. through a suitable orifice. The radiating side edge may be used to ablate tissue and/or assist with cutting and simultaneous sealing of tissue when the spatula has reached its destination.

Herein, microwave energy may have a frequency between 500 MHz and 100 GHz. For example, the spatula may emit microwave radiation in any one or more of the following frequency bands: 900 MHz to 1.5 GHz, 2.2 GHz to 2.45 GHz, 5.725 GHz to 5.875 GHz, 14 GHz to 15 GHz, and 24 GHz to 24.25 GHz. Spot frequencies of 2.45 GHz, 5.8 GHz, or 14.5 GHz may be preferable.

Thus, according to the invention, there may be provided a surgical spatula comprising: a planar transmission line for carrying microwave energy formed from a sheet of a first dielectric material having first and second conductive layers on opposite surfaces thereof, the sheet of first dielectric material having a substantially uniform width dimension of 5 mm or less; a substantially uniform thickness dimension of 2 mm or less; and a substantially uniform length dimension greater than the width dimension; a coaxial cable having an outer diameter of 3 mm or less for delivering microwave energy to the planar transmission line, the coaxial cable comprising an inner conductor, an outer conductor coaxial with the inner conductor, and a second dielectric material separating the outer and inner conductors, the planar transmission line being connected lengthwise to the coaxial cable at a connection interface; and a protective sleeve mounted over the connection interface, wherein one end of the sheet of first dielectric material abuts the end of the coaxial cable at the connection interface, the inner and outer conductors extend beyond the second dielectric at the connection interface to overlap opposite surfaces of the transmission line and electrically contact the first conductive layer and second conductive layer respectively, the first conductive layer is spaced from the end of the transmission line that abuts the coaxial cable to electrically isolate the outer conductor from the first conductive layer, and the width of the first and second conductive layers is selected to create an impedance match between the transmission line and the coaxial cable.

The spatula configuration set forth herein may provide desirable insertion loss between the co-axial feed line and the end radiating section, whilst also providing desirable return loss properties for the edges of the spatula when in contact with air and biological tissue respectively. In more detail, the insertion loss along the structure may be less than 0.2 dB at the frequency of interest, and the return loss less than (more negative than) −3 dB, preferably less than −10 dB. These properties may also indicate a well matched junction between the coaxial cable and the transmission line spatula structure, whereby microwave power is launched efficiently into the spatula. Similarly, when the edges of the spatula are exposed to air or biological tissue that is not of interest, the return loss may be substantially zero (i.e. very little power radiated into free space or undesirable tissue), whereas when in contact with desirable biological tissue the return loss may be less than (more negative than) −3 dB, preferably less than −10 dB (i.e. the majority of power in the spatula is transferred to the tissue). The distal end and both side edges of the spatula may exhibit this effect, i.e. microwave energy may be radiated into tissue from each of the distal end and the side edges.

The substantially uniform thickness dimension of the sheet of first dielectric material may be 1 mm or less, preferably less than 0.7 mm, e.g. 0.61 mm. The thickness of dielectric material influences the impedance of the transmission line and its electrical length.

The power absorption from the end of the spatula with a reduced thickness line is opposite the centre of the dielectric material, whereas with a thicker line the power is concentrated close to the conductive layers. The former configuration may be preferred.

A reduced thickness of material may permit reduction of the width of the first and second conductive layers to achieve a given impedance. This can enable an overall reduction in the width of the device. For example, the substantially uniform width dimension of the sheet of first dielectric material may be 3 mm or less. This width dimension may permit the transmission line to fit down the instrument channel of an endoscope, e.g. for use in minimally invasive surgery. Spatulas having widths greater than 3 mm may still be used in natural orifice transluminal endoscopic surgery (NOTES), whereby the instrument is introduced through a natural orifice within the body.

Using reduced thickness dielectric material and reduced width conductive layers may permit the microwave energy to penetrate deeper into biological tissue.

The planar transmission line may be sandwiched between the inner and outer conductors of the coaxial cable. The inner and outer conductors may be arranged to conform to the surface contour of their respective conductive layers. For example, protruding part of the inner and/or outer conductor may be shaved to create a contact surface that conforms with the respective conductive layer. Alternatively, if braided conductors are used in the coaxial cable, the contact may be made by spreading the cable over its respective conductive layer. The protruding part of the inner conductor may be bent to fit over the first conductive layer.

The protective sleeve may be primarily for supporting the junction between the coaxial cable and the transmission line (spatula structure), e.g. to provide structural integrity when the device is moved within an endoscope and to provide the necessary rigidity when the spatula is used in surgery, i.e. manipulated inside the body. The sleeve may be bonded to the coaxial cable and/or the transmission line, e.g. using glue, solder or the like. The sleeve may be made of plastic, e.g. polypropylene, nylon, polythene or the like. The sleeve may have an outer diameter sized to enable a sliding fit in an endoscope instrument channel. For example, the outer diameter of the sleeve may be 3.1 mm and its thickness may be 0.25 mm. This sleeve may be used with a coaxial cable having an outer diameter of 2.2 mm and a transmission line having a width of 2.6 mm.

To prevent the spatula from coupling energy into the sleeve, the length dimension of the transmission line may be an odd multiple of a quarter wavelength (e.g. one quarter or three quarters of the wavelength or any odd multiple of a quarter wavelength at the frequency of operation) of the microwave energy. The sleeve itself may be up to 20 mm in length.

The sleeve may also prevent microwave energy from radiating outwards into tissue at the junction between the coaxial cable and the transmission line spatula. It would be undesirable for a high percentage of the power at this junction to be coupled into tissue or to generate undesirable heating effects or cause damage to the instrument channel of the endoscope.

The first conductive layer may cover all of one surface of the sheet of first dielectric material except for the isolation spacing at the abutment edge. However, in some embodiments, the width of first conductive layer may be less than the width of the sheet of first dielectric material. However, even in these embodiments it is preferable for the first conductive layer to include an edge coincident with an end of the transmission line opposite the end in abutment with the coaxial cable. In other words, the first conductive layer extends right up to the edge of the sheet of first dielectric material.

The second conductive layer may cover all of one surface of the sheet of first dielectric material. However, similarly to the first conductive layer, its width may be less than the width of the sheet of first dielectric material. Also, similarly to the first conductive layer, it is preferable for the second conductive layer to include an edge coincident with an end of the transmission line opposite the end in abutment with the coaxial cable.

Where the width of the first and/or second conductive layer is less than the width of the sheet of first dielectric material, the first and/or second conductive layers are centrally mounted on the sheet of first dielectric material.

As mentioned above, the first conductive layer is spaced from end of the sheet of dielectric material where it abuts the coaxial cable. The primary purpose of this spacing may be to prevent a short circuit between the inner and outer conductors of the coaxial cable. The spacing may manifest itself as a gap between an edge of the first conductive layer spaced from the end of sheet of first dielectric material in abutment with the coaxial cable. The gap may extend by at least 0.5 mm in the lengthwise direction. The first dielectric material may be exposed in the gap. A secondary purpose of the gap may be to "tune" the spatula for a specific tissue impedance. By varying the size of the gap in the lengthwise direction, the return loss properties of the spatula into a particular type of tissue may also vary. Microwave simulation tools may be used to optimise the gap size to make the spatula suitable for a particular type of tissue. The gap may also be optimised to minimise the insertion loss at the junction with the coaxial cable.

One consequence of a reduced thickness transmission line is that a portion of the end surface of the coaxial cable at the contact interface is not in contact with the sheet of first dielectric material. In preferred embodiments, this portion of the coaxial cable is arranged to taper away from the junction, i.e. the exposed end face of the coaxial cable slopes away from the junction.

The first dielectric material may be Taconic TRF-41 high performance laminate produced by Taconic, which is a low loss ceramic filled PTFE with a high thermal conductivity and low dielectric constant variation with temperature elevation.

The coaxial cable may be a 50Ω coaxial cable such as the UT 85C-LL model made by Micro-Coax, or any other coaxial cable of a similar size, i.e. similar cable assemblies produced by Gore or Huber & Suhner can also be used, with braided inner and outer conductors rather than solid conductors. When choosing cable assemblies, attention should be given to those exhibiting the lowest power loss at the frequency of the microwave energy as it is desirable to minimize cable heating since the length of the cable inside the body may be 2 m or more. High insertion loss also implies that only a small portion of the energy available at the generator will reach the biological tissue, i.e. a system using a 100 W generator, a microwave cable assembly with an insertion loss of 6 dB and a spatula structure with an insertion loss of 3 dB will only deliver 12.5 W of microwave power into the biological tissue structure of interest.

In use, the spatula provides a plurality of edges (the edges of the planar transmission line) which may act as blades suitable for pushing into the stem of a polyp. When this is done, the return loss may be around −10 dB (i.e. 90% of the energy delivered into tissue, which may facilitate tissue ablation to achieve cutting and cauterisation.

The spatula discussed above may have an RF cutting portion integrated therewith. The RF cutting portion may take advantage of the fact that the active and return conductors (or electrodes) are in close proximity to one another, thus a preferential return path may be set up in this manner to enable local tissue cutting action to take place without the need for a remote return pad or a highly conductive liquid, i.e. saline, existing between the two electrodes. In this particular instance, RF energy suitable to cut tissue, e.g. 200-400 V peak to peak delivered in a continuous wave (CW format at 500 kHz, may be coupled into the structure and combined with the microwave ablation energy. The RF cutting portion may thus comprise a RF voltage source (e.g. capable of delivering energy with a frequency between 100 kHz and 500 kHz) coupled to the transmission line and a signal combiner (e.g. duplexer/diplexer unit, frequency diplexer, signal adder or the like), which may include a low pass filter to prevent the high frequency microwave energy from going back into the lower frequency RF energy source and a low pass filter to prevent the lower frequency RF energy from going back into the higher frequency microwave energy source. In one example, the signal combiner may be used to enable the microwave and RF energy sources to be combined at the generator and delivered along a single channel, e.g. co-axial cable, waveguide assembly or twisted pair, to the spatula structure. The RF cutting energy may be delivered solely into the tissue or may be mixed or added with the microwave energy and delivered simultaneously to set up a blended mode of operation. A number of clinically useful tissue effects may be achieved by setting up the system in this manner.

Where both RF energy and microwave energy can be provided via a signal combiner, a portion of the energy delivered to the spatula may be sampled, e.g. using a directional coupler or the like. The sampled energy may be used to control the energy delivery profile, e.g. via a suitably programmed microcontroller of the like.

In a particularly preferred embodiment capable of delivering RF energy, the first dielectric material may be quartz and the first and second conductive layers may each comprise layers of copper and gold.

In another aspect, the disclosure herein provides a surgical spatula having a housing arranged to be securable in the instrument channel of an endoscope, e.g. to facilitate manipulation. The housing may be the sleeve discussed above (referred to as a tube support below). The sleeve may thus both protect the junction between the radiating paddle and coaxial cable and secure the spatula at the distal end of the instrument channel of the endoscope. The device may thus be especially suitable for key-hole surgery, but may also be used in open surgery.

BRIEF DESCRIPTION OF THE DRAWINGS

Examples of the invention are discussed below with reference to the accompanying drawings, in which:

FIG. 12 is simulated side and top view cross-sectional images indicating power absorption when the transmission line or FIG. 11 is pressed into a load;

DETAILED DESCRIPTION; FURTHER OPTIONS AND PREFERENCES

The discussion below describes a spatula for use in ablating polyp stems. A first configuration for use with a frequency of 5.8 GHz is described in detail. A similar design for operation at 14.5 GHz is also briefly described. Finally, a complete embodiment is discussed.

5.8 GHz Embodiment

Figure 1:
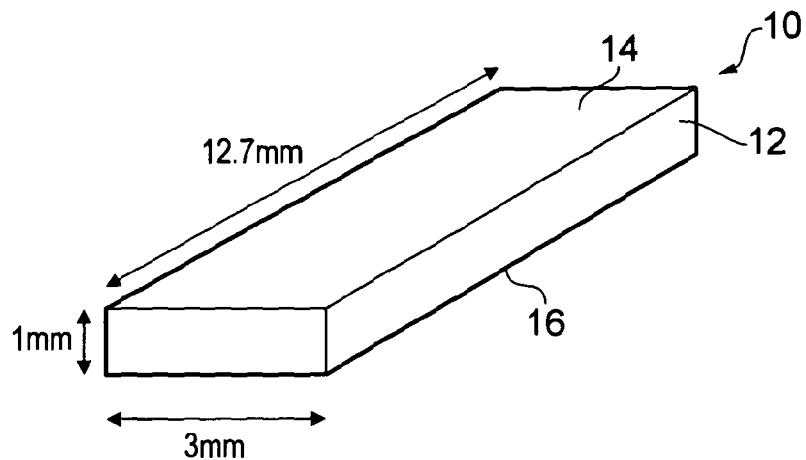
FIG. 1 is a schematic perspective view of a transmission line for use in a spatula according to one embodiment of the invention.

FIG. 1 shows a planar transmission line 10 comprising a block of first dielectric material 12 having an upper conductive layer 14 on a top surface thereof and a lower conductive layer 16 on a bottom surface thereof. The material chosen for the first dielectric material was Taconic TRF-41. This is a slightly lower loss version of RF-41, which is described as a low-loss alternative to FR-4 (a standard PCB material for lower frequencies). RF-41 has a dielectric constant of 4.1 and a loss tangent of 0.0038 at 10 GHz. It is claimed to have stable dielectric constant and loss over frequency. TRF-41 has a dielectric constant of 4.1 and a loss tangent of 0.0035. These values were used in the simulations. At 5.8 GHz the wavelength in TRF-41 is 25.4 mm.

Initial simulations were of a slab of TRF-41 12.7 mm long (half a wavelength), 3 mm wide and 1 mm thick, coated with 0.018 mm copper on the top and bottom surfaces to create the conductive layers 14, 16. The copper is a standard thickness taken from the TRF-41 datasheet. The standard dielectric thicknesses are shown below. The difference between 1 mm thickness and 1.02 mm is not significant in the context of this application.

| Dielectric Thickness | |
| --- | --- |
| inches | mm |
| 0.0080 | 0.2 |
| 0.0160 | 0.41 |
| 0.0240 | 0.61 |
| 0.0320 | 0.81 |
| 0.0400 | 1.02 |
| 0.0640 | 1.63 |
| 0.1200 | 3.05 |

The metallised dielectric forms a transmission line which can propagate a wave in a hybrid mode between the two metal plates. The energy is largely concentrated in the dielectric.

In a first simulation, the fundamental mode (at 5.8 GHz) was launched under ideal conditions into one end of the transmission line.

Figure 2:
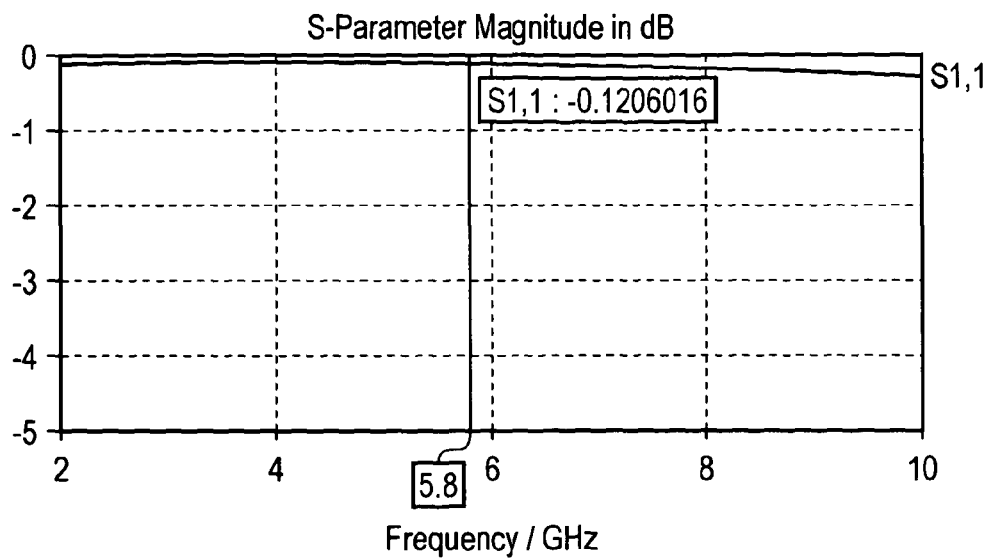
FIG. 2 is a graph showing the return loss into air of the transmission line shown in FIG. 1, assuming ideal microwave energy feed conditions.

The impedance of the transmission line is 48Ω, and the return loss into air, shown in FIG. 2, is −0.12 dB. This is very good, as it means that if the spatula is not touching any object, very little power (less than 3%) will leak out.

Figure 3:
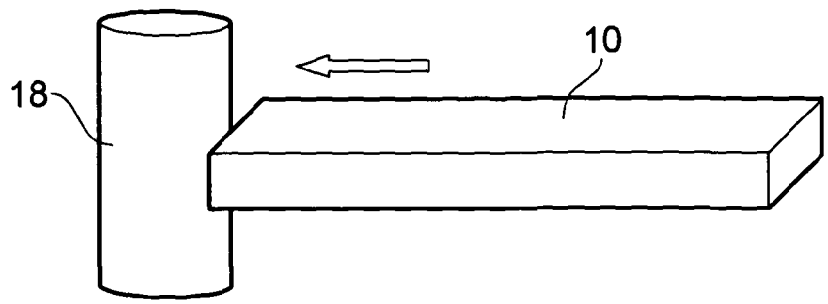
FIG. 3 is a schematic perspective view of the transmission line shown in FIG. 1 in contact with a cylindrical load.

In order to judge how well the spatula would deliver power into a polyp, a cylindrical load 2 mm in diameter was modelled. The load was long enough so that the end effects were not significant, in fact, it may be seen that power absorption is concentrated near to the end of the spatula, so the length of the load is actually immaterial. FIG. 3 shows the transmission line 10 abutting the load 18.

The load 18 was given a dielectric constant of 27.222 and a loss tangent of 14.448. These are only estimated values and tests should be repeated with more accurate parameter values if they differ greatly from these.

Figure 4A:
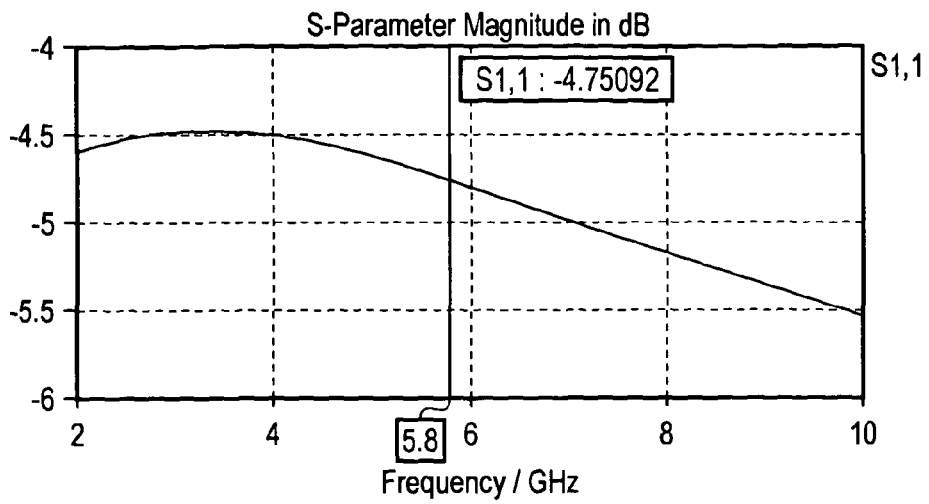
FIG. 4A is a graph showing the return loss into the load when the transmission line is touching the load.
Figure 4B:
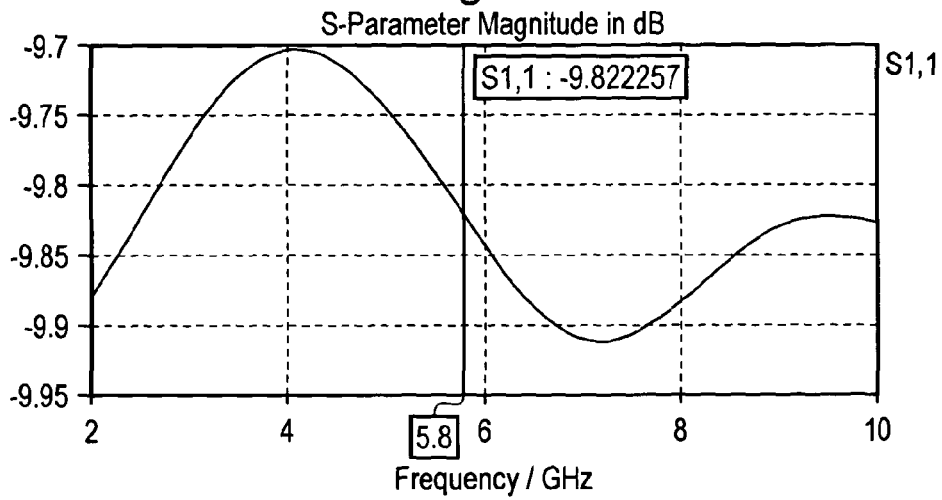
FIG. 4B is a graph showing the return loss into the load when the transmission line is pressed into the load by 0.3 mm.
Figure 4C:
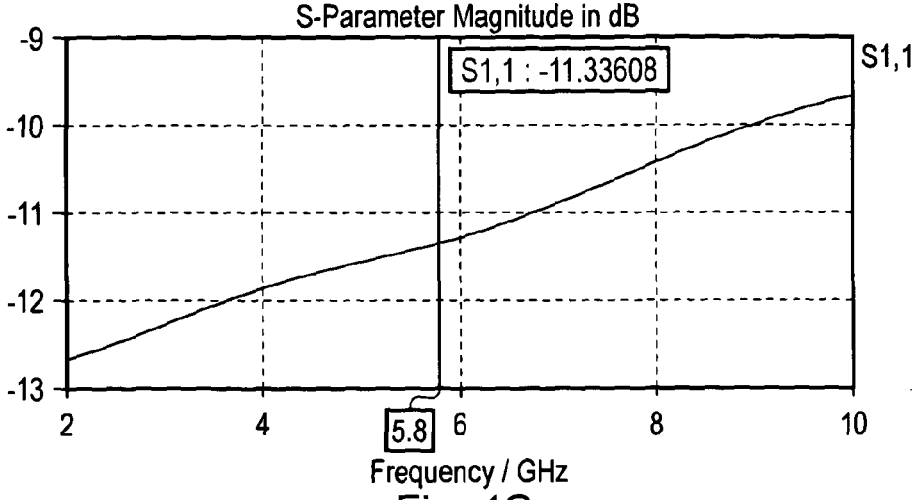
FIG. 4C is a graph showing the return loss into the load when the transmission line is pressed into the load by 0.7 mm.

The return loss with the load just touching the end of the spatula is 4.75 dB, i.e. about one third of the power is reflected, as shown in FIG. 4A. If the spatula is pressed into the load slightly by 0.3 mm and 0.7 mm, the return loss improves to 9.8 and 11.3 dB respectively, as shown in FIGS. 4B and 4C respectively.

Figure 5A:
FIG. 5A is simulated side and top view cross-sectional images indicating power absorption when the transmission line is touching the load.
Figure 5B:
FIG. 5B is simulated side and top view cross-sectional images indicating power absorption when the transmission line is pressed into the load by 0.3 mm.
Figure 5C:
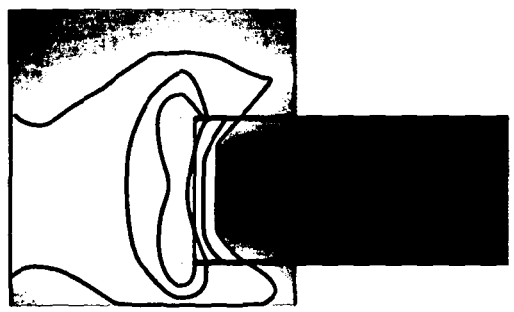
FIG. 5C is a simulated side view cross-sectional image indicating power absorption when the transmission line is pressed into the load by 0.7 mm.

The pattern of the absorption of power in the load in each case is shown in FIGS. 5A to 5C. For all three a centre cross-section seen from the side is shown for each, and a cross-section from above at a plane close to (or in) the top conductor is shown for the first two. The side views show that power absorption occurs close to the conductive layers.

Figure 6A:
FIG. 6A is a simulated top view cross-sectional image indicating power absorption when a side edge of the transmission line contacts the load at a first position.
Figure 6B:
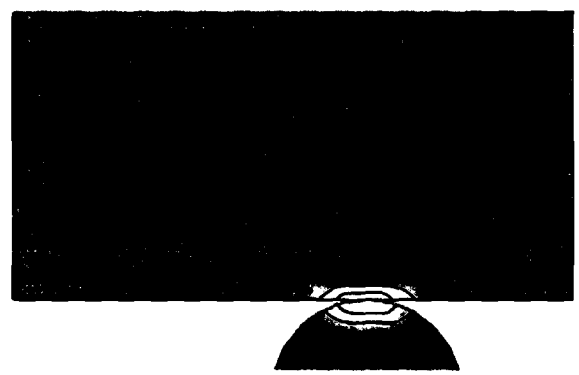
FIG. 6B is a simulated top view cross-sectional image indicating power absorption when a side edge of the transmission line contacts the load at a second position.
Figure 6C:
FIG. 6C is a simulated top view cross-sectional image indicating power absorption when a side edge of the transmission line contacts the load at a third position.
Figure 7A:
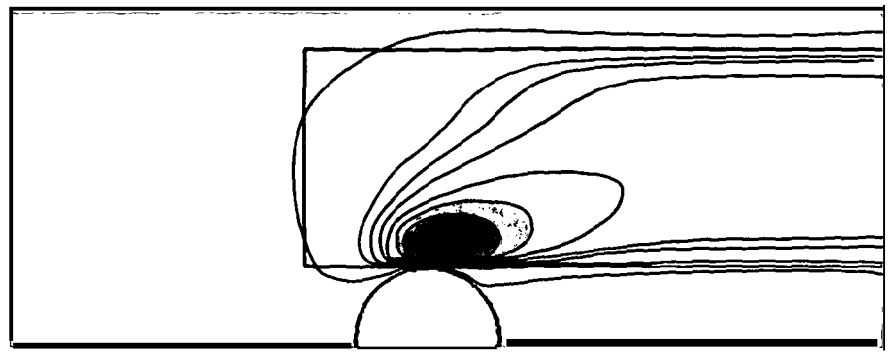
FIG. 7A is a simulated top view cross-sectional image indicating power flow when a side edge of the transmission line contacts the load at a first position.
Figure 7B:
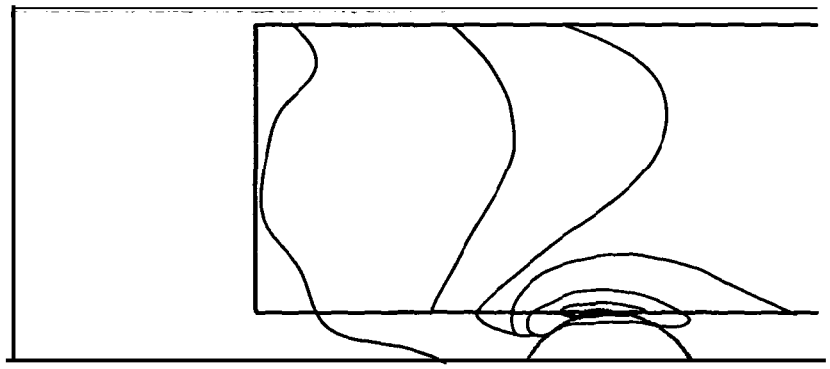
FIG. 7B is a simulated top view cross-sectional image indicating power flow when a side edge of the transmission line contacts the load at a second position.
Figure 7C:
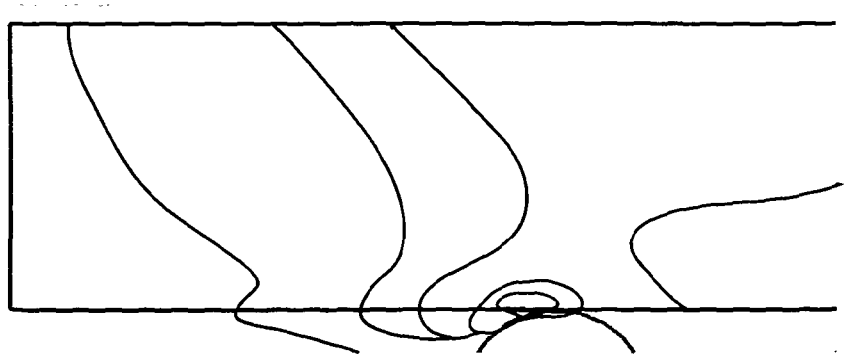
FIG. 7C is a simulated top view cross-sectional image indicating power flow when a side edge of the transmission line contacts the load at a third position.
Figure 8A:
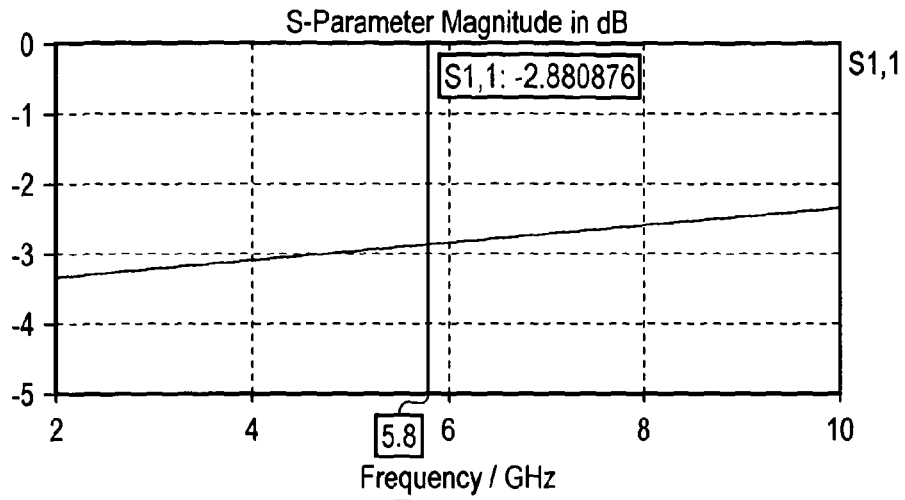
FIG. 8A is a graph showing the return loss into the load when a side edge of the transmission line contacts the load at a first position.
Figure 8B:
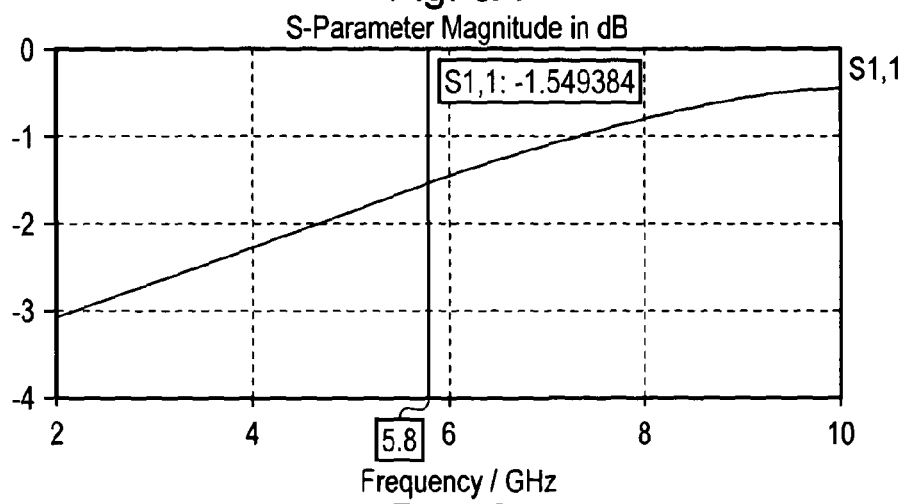
FIG. 8B is a graph showing the return loss into the load when a side edge of the transmission line contacts the load at a second position.
Figure 8C:
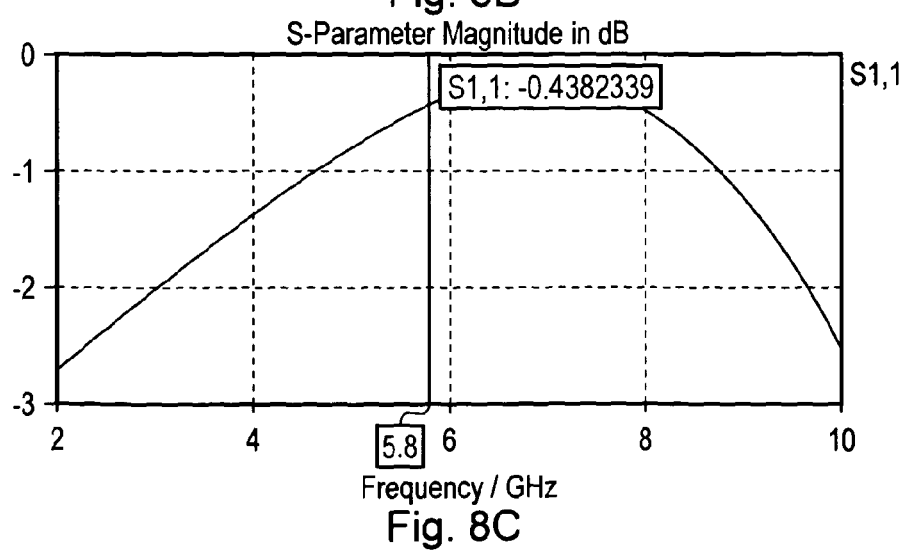
FIG. 8C is a graph showing the return loss into the load when a side edge of the transmission line contacts the load at a third position.

Simulations were carried out with the load put at the side of the spatula, at different distances (1.7 mm, 3.7 mm, 5.7 mm and 9.7 mm) back from the end opposite the energy launch plane. In FIGS. 6A to 6C, the position of the load is shown; the power is fed to the spatula from the right hand side of the drawings. FIGS. 6A to 6C show the power absorption in each case, viewed in cross section from above. FIGS. 7A to 7C show power flow for the same cross-sectional views. FIGS. 8A to 8C are graphs showing the return loss for each situation. The return loss is optimal when the load is near the distal end of the spatula, and worsens as the load moves back, until the load is more than a quarter wavelength back, when the return loss improves again.

As is the case when the load is at the end of the spatula, the power coupling is not very strong when the spatula is just touching the load. 3 dB return loss means that only half the incident power is absorbed, and the other half returns to the generator, less some losses in the feed and cables.

Figure 9A:
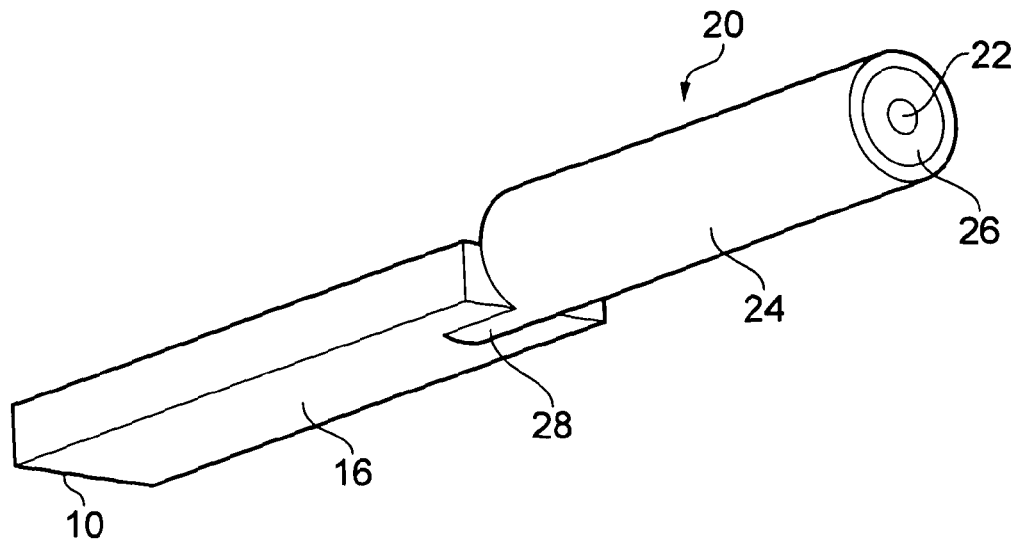
FIG. 9A is a schematic rear perspective view of a surgical spatula according to an embodiment of the invention.
Figure 9B:
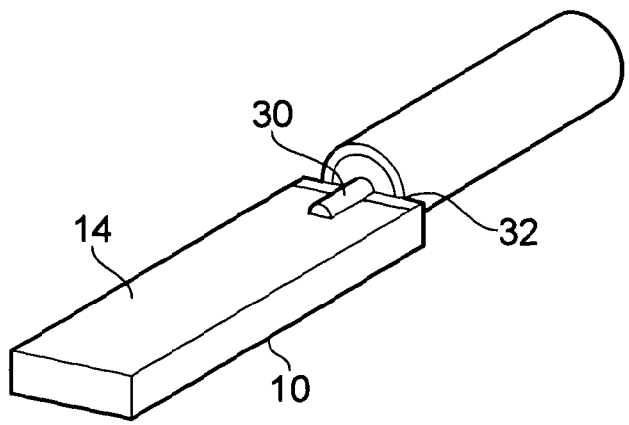
FIG. 9B is a schematic front perspective view of the spatula shown in FIG. 9A.
Figure 9C:
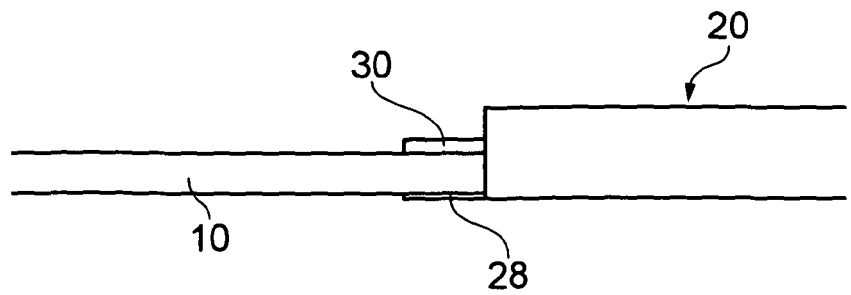
FIG. 9C is a schematic side view of the spatula shown in FIG. 9A.

FIGS. 9A to 9C show the feed arrangement for the transmission line 10 from different directions. The spatula can be end-fed using a 50Ω coaxial cable 20. The coaxial cable modelled is UT 85C-LL (Micro-Coax). The coaxial cable comprises an inner conductor 22, an outer conductor 24 and a dielectric material 26 separating the inner and outer conductors 22, 24. At the distal end of the coaxial conductor 20, the inner and outer conductors 22, 24 have protruding portions 28, 30 which extend away from the dielectric material 26. The transmission line 10 is sandwiched between the protruding portions 28, 30 so that its proximal end abuts the distal end of the coaxial cable. The protruding portion 30 of the inner conductor is arranged to contact the upper conductive layer 14 and the protruding portion 28 of the outer conductor is arranged to contact the lower conductive layer 16. This kind of join can be easily made with standard braided coaxial cable. Small deviations in the shape of the outer conductor at the join should not make much difference to the insertion loss. In a braided conductor the bottom joint could be more spread out which may be advantageous. The centre conductor can be bent to fit over the top conductor, rather than shaved.

A gap 32 is provided between the proximal edge of the upper conductive layer and the distal end of the coaxial cable to prevent shorting between the inner and outer conductors.

Figure 10:
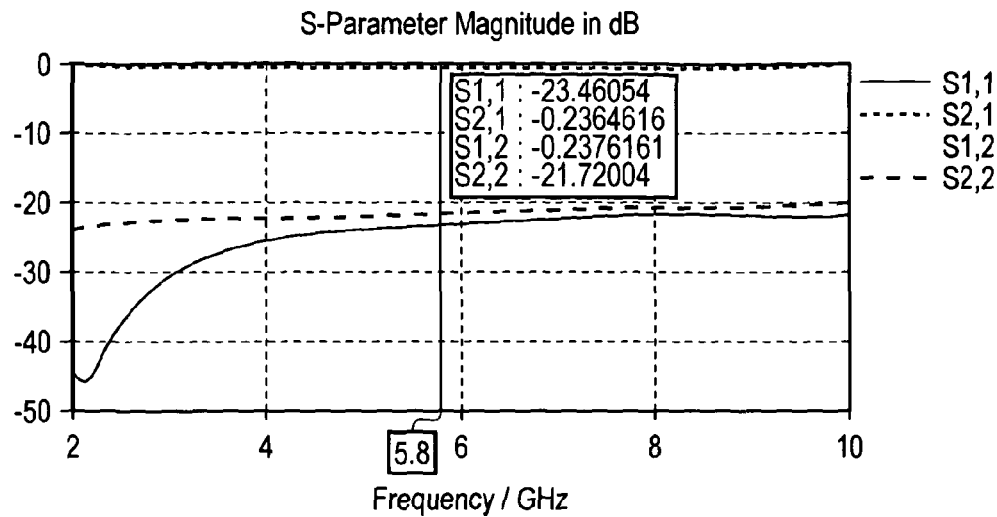
FIG. 10 is a graph showing the insertion loss and return loss of the junction between the coaxial cable and planar transmission line in the surgical spatula when the end transmission line is in contact with a load.

The return loss and insertion loss of this junction arrangement when the spatula is touching a load is shown in FIG. 10. The return loss is better than −20 dB and the insertion loss about −0.24 dB, both of which are excellent. The feed from coaxial cable does not introduce any significant loss at this frequency.

All the previous drawings show results for a spatula thickness of 1 or 1.02 mm.

Figure 11:
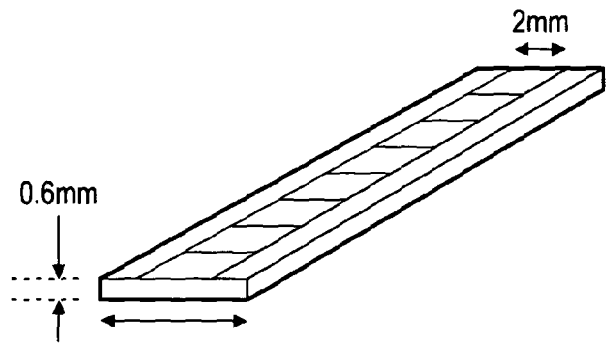
FIG. 11 is a schematic perspective view of a transmission line for use in a spatula according to another embodiment of the invention.

FIG. 11 shows a transmission line similar to that of FIG. 1 except that the thickness is 0.6 mm. If the thickness of the spatula is reduced, the track width can also be reduced while keeping the impedance close to 50Ω. The width of the conductor layers in this example is less than the width of the sheet of dielectric material. As shown in FIG. 11, the width of the conductive layer is 2 mm, on top and bottom surfaces. The impedance of this structure is 43Ω (for 50Ω the width of the conductor track should be reduced to 1.8 mm).

A reduced track width (1.8 mm) is attractive because it will fit inside a 3.1 mm outer diameter plastic tube (not shown).

This tube will help to support the joint between the cable and the spatula, and can be glued to the cable behind the joint, and perhaps to the sides of the spatula. The tube could be 10 mm or 20 mm long, for example. The tube will also be a good, but sliding, fit in the endoscope tube, so that the spatula position can be positively controlled by the endoscope.

Figure 12:
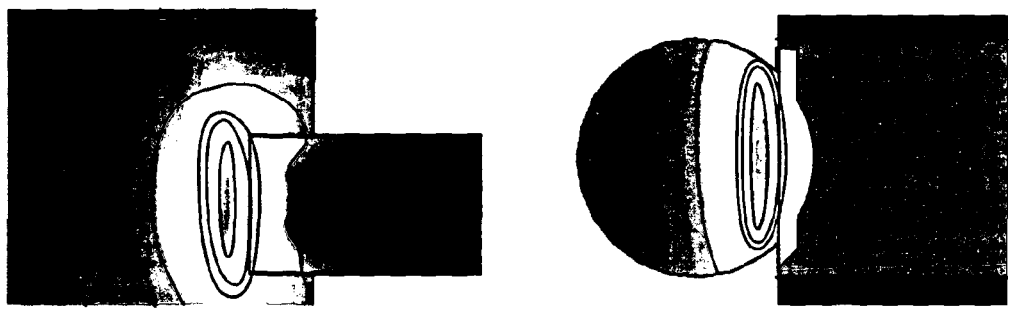

FIG. 12 shows the power absorption in the load, from the side and the top. It can be seen that the power absorption from this thinner spatula appears to be opposite the centre of the dielectric, rather than concentrated close to the conductors as it is with the thicker spatula. This is probably a better distribution of the absorbed power and seems to penetrate more deeply, which is attractive.

The discussion above, demonstrates that a spatula fed from a thin co-axial cable can deliver power effectively to a 2 mm diameter load, similar to a polyp. It is recommended that a 0.61 mm thick dielectric should be used with a track width of 1.8 mm.

In use, a lower frequency (e.g. in the range 100 kHz to 500 kHz) is selectively connectable to the spatula via the same transmission line. The lower frequency energy assists in cutting through the stem of the polyp. The higher frequency (i.e. 5.8 GHz) energy acts primarily to coagulate the stem to prevent fluid (e.g. blood) loss. Both frequencies may be applied simultaneously. The "reach" (i.e. depth of penetration) of the coagulation energy may be arranged to be greater than (e.g. twice) that of the cutting energy, so that coagulation has already occurred at the tissue being cut.

14.5 GHz Embodiment

Following the work described above on the spatula for 5.8 GHz, the same design was tested at 14.5 GHz. The same size of dielectric slab (1 mm by 3 mm by 12.7 mm) and co-axial cable were used, and the same geometry at the join.

Figure 13:
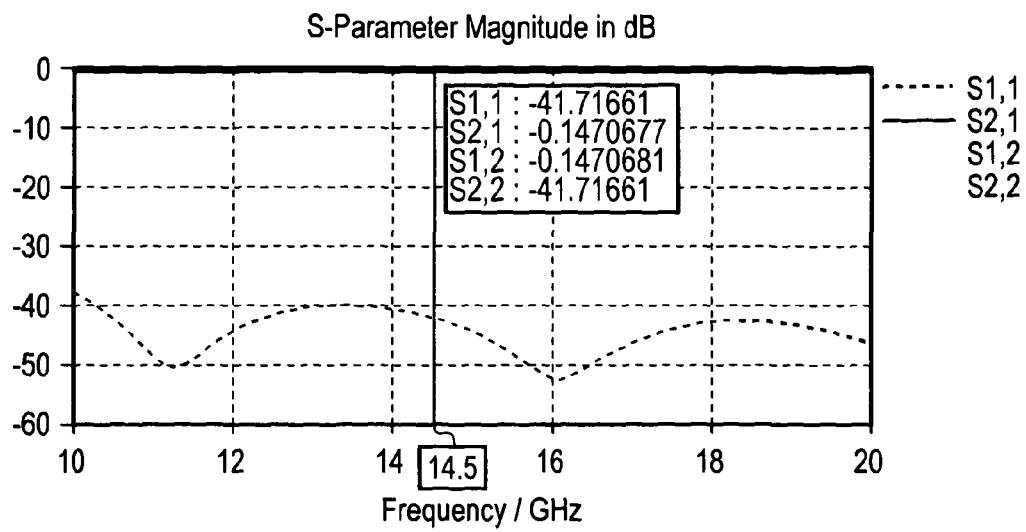
FIG. 13 is a graph showing the insertion loss and return loss through the transmission line shown in FIG. 11 when in contact with a load and assuming ideal microwave energy feed conditions.

The loss through the 12.7 mm transmission line is shown in FIG. 13, i.e. about −0.15 dB, which is insignificant. The return loss is also very good as should be expected of a short length of transmission line matched at both ends. The main point is that transmission loss in the dielectric is very low at 14.5 GHz, with only 1.5% of the power being absorbed in this length.

The coupling of a bare transmission line into a 2 mm load was also modelled. The return loss was about 5.4 dB, which is better than at 5.8 GHz. The power loss density shows that the loss is concentrated around the metal edges, even more so than at 5.8 GHz. When used at higher frequencies, it may therefore be beneficial to use a thinner transmission line, i.e. 0.6 mm thick rather than 1 mm thick.

A feed from coaxial cable to the spatula was modelled, using the same size as for 5.8 GHz. However, in this case the insertion loss was −1.15 dB, which is high enough to be potentially of concern. This loss means that 23% of the input power is lost on the way through the junction. The value of the return loss was such that less than 5% of the power was reflected back, and since it is expected that about 2 or 3% may be absorbed in the coaxial cable and transmission line, about 15% may be either dissipated in the coaxial cable and spatula or radiated away. This could cause unwanted heating and irradiation.

Power flow simulations of the junction indicated that there is power flow out of the top face of the end of the coaxial cable, in particular a significant upward component of power flow radiating away from the spatula.

Figure 14:
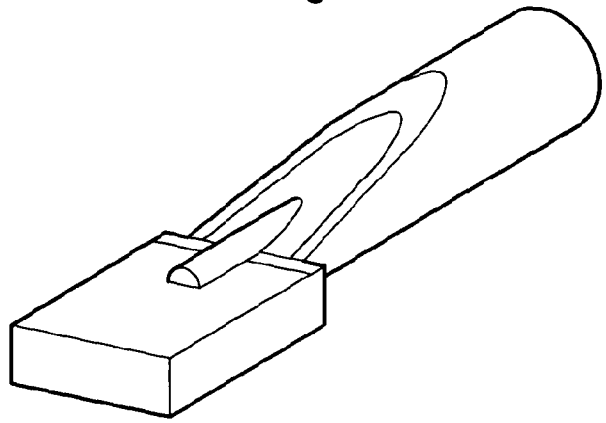
FIG. 14 is a schematic front perspective view of a surgical spatula according to another embodiment of the invention.

To reduce the radiation from the end face of the coaxial cable, the arrangement illustrated in FIG. 14 was conceived, in which the exposed end surface of the coaxial cable tapers away from the junction. Simulations indicate that the radiation reduces with increasing taper. FIG. 14 illustrates an 80° taper.

Figure 15:
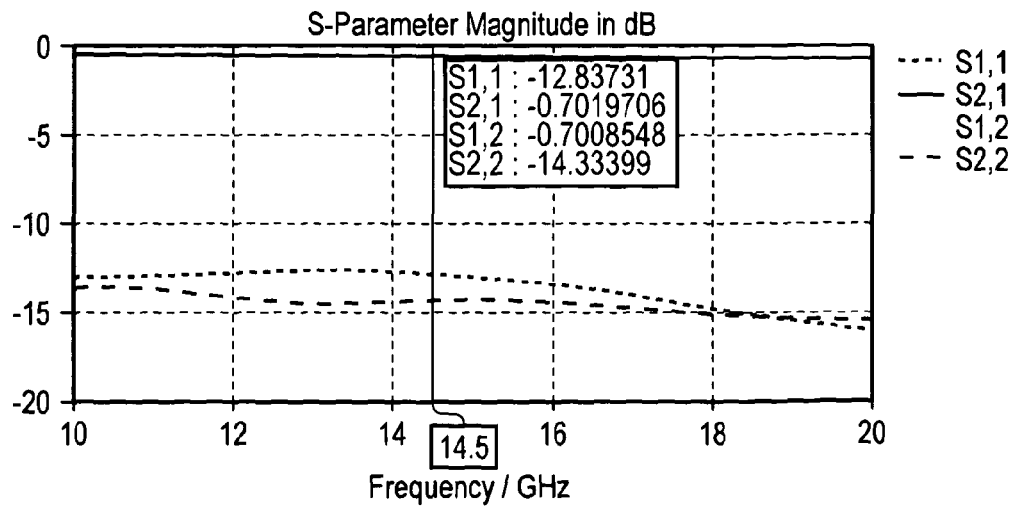
FIG. 15 is a graph showing the insertion loss and return loss of the junction between the coaxial cable and planar transmission line in the surgical spatula when the end transmission line is in contact with a load.

FIG. 15 is a graph showing loss at the junction. The return loss is about −13 dB, so that 5% of the power is reflected, but the insertion loss is now −0.7 dB. This corresponds to a loss of about 15% of the power, indicating that no more than 8% is radiated.

Thus, a similar design to that used at 5.8 GHz will work at 14.5 GHz. A well matched junction to coaxial cable can be achieved, but a taper to the top of the coaxial cable is desirable to reduce radiation from the joint. As for 5.8 GHz, the penetration of power into a load will be better for a 0.6 mm thick transmission line.

However, the performance of the 5.8 GHz spatula is expected to be superior in terms of having a deeper penetration depth and in having less radiation from the joint to co-axial cable. In addition, losses in the feed cable will be lower at 5.8 GHz than at 14.5 GHz.

Although the simulations were done using TRF-41 dielectric material for the transmission line, RF-41 may also be suitable.

Complete Spatula

Figure 16:
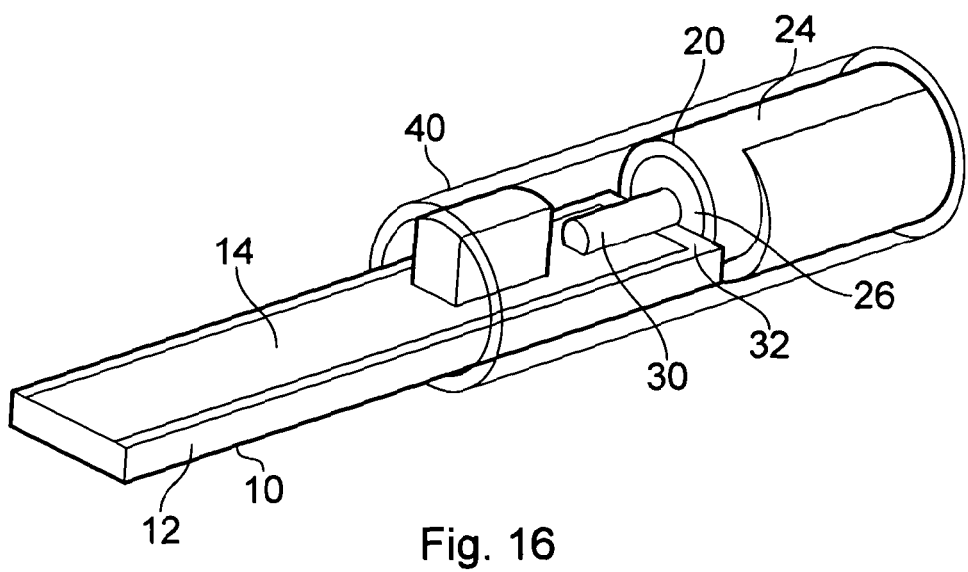
FIG. 16 is a schematic top perspective view of a surgical spatula according to another embodiment of the invention.
Figure 17:
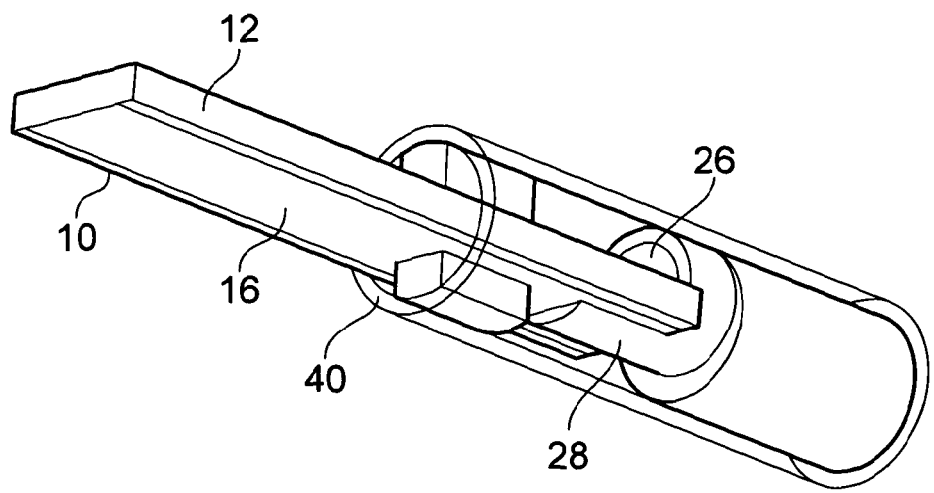
FIG. 17 is a schematic bottom perspective view of the spatula shown in FIG. 16.

FIGS. 16 and 17 illustrate views of a complete embodiment of the surgical spatula according to the invention. This embodiment has a 0.6 mm thick transmission line 10 connected to a coaxial cable 20 as discussed above. Common components are given the same reference numbers and are not described again. The spatula in this embodiment is suitable for operation at 2.45 GHz, 5.8 GHz and 14.5 GHz.

In FIGS. 16 and 17 a plastic tube support 40 (shown as translucent for convenience) is mounted over the junction between the transmission line 10 and the coaxial cable 20. The inner diameter of the tube support 40 is greater than the outer diameter of the coaxial cable 20 to enable it to be fitted over the cable. A mounting structure 42, e.g. glue or the like, is attached between the coaxial cable 20 and the tube support 40 to secure the cable in place. Similarly, mounting blocks 44, 46 (e.g. glue) are attached between the transmission line 10 and the tube support 40 to secure the transmission line in place.

The transmission line comprises a 0.61 mm thick sheet 12 of TRF-41 (dielectric constant 4.1 and loss tangent 0.0035). The coaxial cable 20 has an outer diameter of about 2.2 mm and a pin diameter of 0.574 mm. The coaxial cable 20 used in the model is UT 85C-LL (from Micro-Coax).

The conductive layers 14, 16 on the transmission line 12 go right to the end of the sheet 12 and are 2.002 mm wide. The sheet 12 is 2.6 mm wide.

The tube support 40 is a polypropylene tube having an outer diameter of 3.1 mm, to be a good sliding fit in an endoscope, and inner diameter of 2.6 mm. This gives a wall thickness of about 0.25 mm. The material and thickness is not critical; nylon or polythene may be used, or a number of other plastics. The edges of the transmission line may be chamfered so that the spatula will sit in place just below the diameter of the tube.

The tube comes 5 mm along the length of the transmission line 10. The overlap with the coaxial cable is 5 mm here but can be as long as required. The tube may be short enough to get through a bent endoscope. The main purpose of the tube is to support the spatula and to hold it steady in the end of the endoscope.

The mounting structure 42 and mounting blocks 44, 46 may be made of almost anything that works to hold things in place, as they do not affect the performance of the device if kept away from the spatula edges and the pin of the coax.

The gap 32 between the upper conductive layer 14 and the coaxial cable is 0.5 mm as shown above.

The centre of the spatula is offset by about 0.5 mm (0.53 mm) from the centre of the coaxial cable. The axis of the outer tube is about 0.3 mm above the centre of the spatula, but basically only needs to fit over things and hold them steady.

The dielectric sheet 12 may be just over one quarter or three quarters of a wavelength long (e.g. 8 mm or 21 mm) so that a standing wave will not couple strongly to a supporting plastic tube near the base of the spatula.

Fixing Relative to an Endoscope

The detailed disclosure above refers to a surgical spatula configuration (radiating paddle and coaxial feed cable) having a size that makes them suitable for travelling down the instrument channel of an endoscope. In use, this allows insertion of the spatula to a treatment site from a proximal end of an endoscope. When the spatula arrives at the distal end, it is desirable for it to be secured relative to the endoscope, e.g. to facilitate manipulation. In another aspect of the invention, the tube support can be used to achieve this securing function. The tube support may thus both protect the junction between the radiating paddle and coaxial cable and secure the spatula at the distal end of the endoscope.

In one embodiment of this idea, the tube support may be radially expandable to provide an interference fit in the endoscope instrument channel. For example, the tube support may be arranged to change shape or may include expanding portions, e.g. that can be activated by control signals sent along the endoscope.

In one embodiment, the tube support may be made from a material that changes shape with an applied voltage or current, i.e. a piezoelectric material (applied voltage to change shape) or magnetostrictive material (applied current to change shape). The tube support may return to its original shape when voltage/current is removed to enable the radiating structure and the microwave cable to be removed from the instrument channel of the endoscope. The tube support may be made from a low loss microwave material to ensure that the microwave field is not absorbed into this material.

In another embodiment, the tube support may be arranged to engage a cooperating structure located at the distal end of the endoscope instrument channel. The cooperating structure may be another tube, inserted into and secured with respect to the distal end of the endoscope instrument channel.

The tube support may provide the mechanical strength and electrical properties necessary to ensure that junction cannot be damaged and that the microwave power is not lost, and the second tube may be sized to permit the radiating paddle to fit through it but to lock with the tube support. The locking function may be achieved by an interference fit, e.g. aided by mating tapered surfaces, or by interlocking formations on the tube support and second tube.

The invention claimed is:

1. A surgical spatula comprising:
    a planar transmission line for carrying microwave energy formed from a sheet of a first dielectric material having first and second conductive layers on opposite surfaces thereof, the sheet of first dielectric material having
        a substantially uniform width dimension of 5 mm or less;
        a substantially uniform thickness dimension of 2 mm or less; and
        a substantially uniform length dimension greater than the width dimension;
    a coaxial cable having an outer diameter of 3 mm or less for delivering microwave energy to the planar transmission line, the coaxial cable comprising an inner conductor, an outer conductor coaxial with the inner conductor, and a second dielectric material separating the outer and inner conductors, the planar transmission line being connected lengthwise to the coaxial cable at a connection interface; and
    a protective sleeve mounted over the connection interface, wherein
        one end of the sheet of first dielectric material abuts the end of the coaxial cable at the connection interface,
        the inner and outer conductors extend beyond the second dielectric at the connection interface to overlap opposite surfaces of the transmission line and electrically contact the first conductive layer and second conductive layer respectively,
        the first conductive layer is spaced from the end of the transmission line that abuts the coaxial cable to electrically isolate the outer conductor from the first conductive layer, and
        the width of the first and second conductive layers is selected to create an impedance match between the transmission line and the coaxial cable.

2. A surgical spatula according to claim 1, wherein the substantially uniform thickness dimension of the sheet of first dielectric material is 1 mm or less, preferably less than 0.7 mm.

3. A surgical spatula according to claim 1, wherein the substantially uniform width dimension of the sheet of first dielectric material is 3 mm or less.

4. A surgical spatula according to claim 1, wherein the inner conductor has a contact surface that conforms with the first conductive layer in the region of contact therebetween.

5. A surgical spatula according to claim 1, wherein the outer conductor has a contact surface that conforms with the second conductive layer in the region of contact therebetween.

6. A surgical spatula according to claim 1, wherein the sleeve is bonded to the coaxial cable and/or the transmission line.

7. A surgical spatula according to claim 1, wherein the sleeve is made of plastic.

8. A surgical spatula according to claim 1, wherein the sleeve has an outer diameter sized to enable a sliding fit in an endoscope instrument channel.

9. A surgical spatula according to claim 1, wherein the first conductive layer includes an edge coincident with an end of the transmission line opposite the end in abutment with the coaxial cable.

10. A surgical spatula according to claim 1, wherein the second conductive layer includes an edge coincident with an end of the transmission line opposite the end in abutment with the coaxial cable.

11. A surgical spatula according to claim 1, wherein the width of first and/or second conductive layers is less than the width of the sheet of first dielectric material.

12. A surgical spatula according to claim 11, wherein the first and/or second conductive layer is centrally mounted on the sheet of first dielectric material.

13. A surgical spatula according to claim 1, wherein the first conductive layer has an edge spaced by at least 0.5 mm from the end of sheet of first dielectric material in abutment with the coaxial cable.

14. A surgical spatula according to claim 1, wherein the length dimension of the transmission line is ¼ or ¾ of the wavelength of the microwave energy.

15. A surgical spatula according to claim 1, wherein the frequency of the microwave energy is 2.45, 5.8, or 14.5 GHz.

16. A surgical spatula according to claim 1 sized to travel within an endoscope instrument channel.

17. A surgical spatula according to claim 1, wherein a portion of the end surface of the coaxial cable not in contact with the sheet of first dielectric material at the connection interfaces tapers outwardly away from the connection interface.

* * * * *